Figure 1:
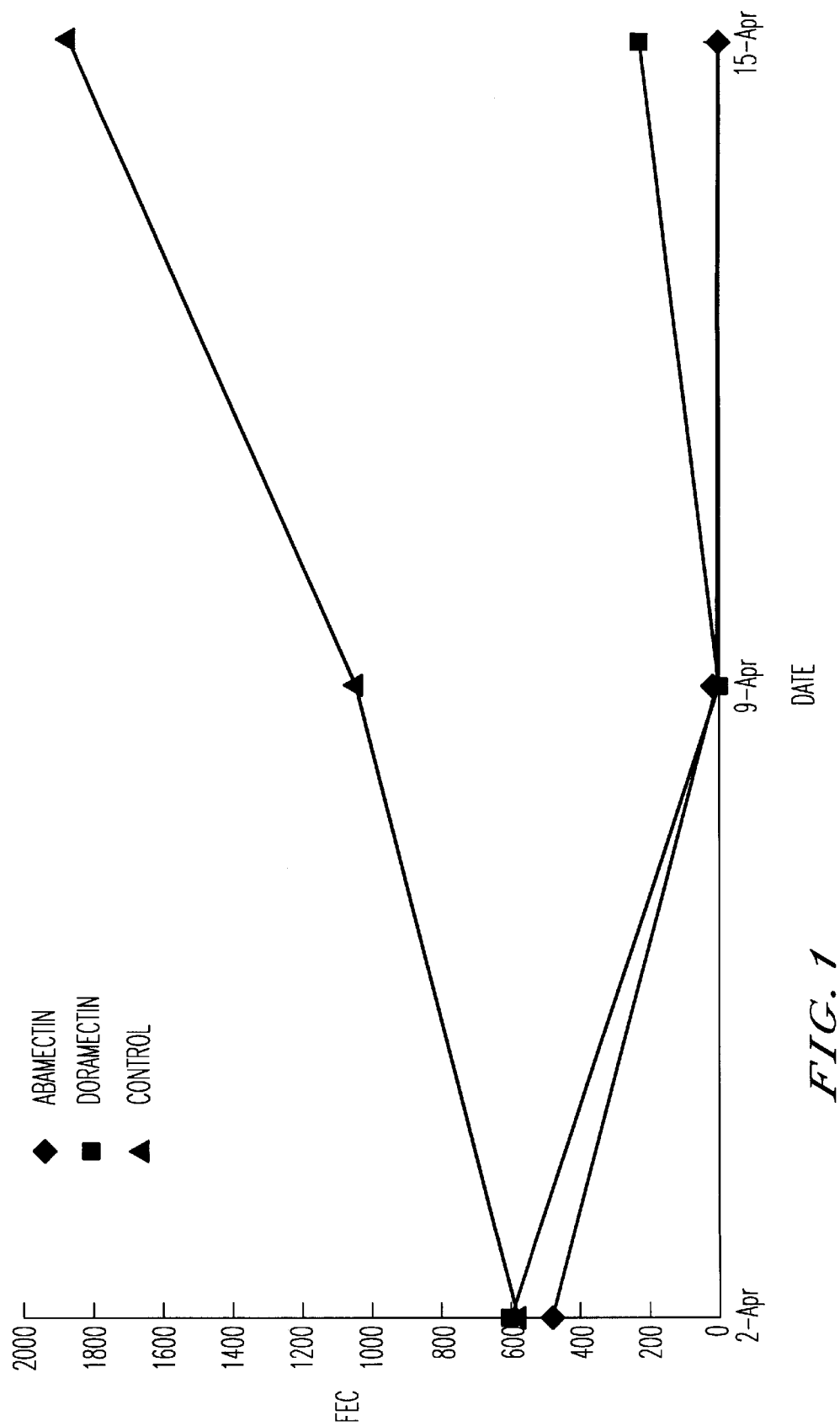

United States Patent [19]

Harvey

[11] Patent Number: 6,013,636
[45] Date of Patent: Jan. 11, 2000

[54] ANTHELMINTIC MACROCYCLIC LACTONE COMPOSITIONS

[75] Inventor: Colin Manson Harvey, Auckland, New Zealand

[73] Assignee: Ashmont Holdings Limited, Auckland, New Zealand

[21] Appl. No.: 09/043,569

[22] PCT Filed: Sep. 19, 1996

[86] PCT No.: PCT/NZ96/00099

§ 371 Date: Mar. 25, 1998

§ 102(e) Date: Mar. 25, 1998

[87] PCT Pub. No.: WO97/11709

PCT Pub. Date: Apr. 3, 1997

[30] Foreign Application Priority Data

Sep. 25, 1995 [NZ] New Zealand ............... 280085
Sep. 29, 1995 [NZ] New Zealand ............... 280134
Jul. 26, 1996 [NZ] New Zealand ............... 280134

[51] Int. Cl.$^7$ ................................................. A61K 31/70
[52] U.S. Cl. .................................................. 514/30
[58] Field of Search .................................................. 514/30

[56] References Cited

U.S. PATENT DOCUMENTS

| 4,916,120 | 4/1990 | Röben et al. | 514/30 |
| 5,674,897 | 10/1997 | Kim et al. | 514/552 |
| 5,756,474 | 5/1998 | Furstenau | 514/30 |
| 5,773,422 | 6/1998 | Komer | 514/30 |

FOREIGN PATENT DOCUMENTS

| 12076/83 | 9/1983 | Australia . |
| 27505/88 | 7/1989 | Australia . |
| 215313 | 8/1986 | European Pat. Off. . |
| 254978 | 7/1987 | European Pat. Off. . |
| 503538 | 3/1992 | European Pat. Off. . |
| 2283677 | 5/1995 | United Kingdom . |
| WO 93/03751 | 3/1993 | WIPO . |
| 9505812 | 3/1995 | WIPO . |

*Primary Examiner*—Kevin E. Weddington
*Attorney, Agent, or Firm*—Oblon, Spivak, McClelland, Maier & Neustadt, P.C.

[57] ABSTRACT

A composition comprising an anthelmintic chosen from the class of macrocyclic lactones including but not limited to the avermectins, ivermectin, doramectin, abamectin, milbemycin and moxidectin, together with a vegetable oil and a co-solvent chosen from the group comprising alcohols having four or more carbons atoms. The compositions of the inventions may be formulated as injections, drenches or for topical administration and are suitable for treating helminthiasis in animals.

10 Claims, 2 Drawing Sheets

ANTHELMINTIC MACROCYCLIC LACTONE COMPOSITIONS

TECHNICAL FIELD OF THE INVENTION

This invention relates to compositions containing an anthelmintic chosen from the class of macrocyclic lactones including but not limited to the avermectins, ivermectin, doramectin, abamectin, milbemycin and moxidectin.

BACKGROUND

This class of anthelmintics are difficult to formulate. For example, the commercially available injectable antiparasitic agent based on an aqueous co-solvent formulation containing ivermectin, water and an organic co-solvent, has been shown to result in some precipitation of the ivermectin at the injection site, with the possibility of irritation to the animal, and possible loss of effectiveness as an anthelmintic. In pour-on formulations, water miscible formulations are diluted if there is rain after treatment.

OBJECT

It is an object of this invention to provide an improved injectable composition containing an anthelmintic, or one which will at least provide the public with a useful choice.

STATEMENT OF INVENTION

One aspect of the invention provides an injectable solution containing an anthelmintic chosen from the class of macrocyclic lactones including but not limited to the avermectins, ivermectin, doramectin, abamectin, milbemycin, and moxidectin, together with a vegetable oil and a co-solvent chosen from the group comprising alcohols having 4 or more carbon atoms.

Preferred alcohols are benzyl alcohol, ethyl benzyl alcohol, phenethyl alcohol and other aromatic monohydric alcohols.

The most preferred co-solvent is benzyl alcohol. More preferably the benzyl alcohol is present in the range of 1–30% by weight.

Preferred vegetable oils are soya bean oil, sesame oil and corn oil.

The most preferred oil is soya bean oil.

Preferably the anthelmintic is chosen from the group comprising abamectin and ivermectin.

More preferably the abamectin or ivermectin is present in the range from 0.5–5% by weight of the formulation.

Optionally, a wetting agent such as ethyl oleate may be used to assist in dissolving the anthelmintic in solution.

Optionally, oil soluble vitamins may be added.

In another aspect the invention provides a pour-on composition containing an anthelmintic chosen from the class of macrocyclic lactones including but not limited to the avermectins, ivermectin, doramectin, abamectin, milbemycin, and moxidectin, together with a vegetable oil and a co-solvent chosen from the group comprising alcohols having 4 or more carbon atoms.

Preferred alcohols are benzyl alcohol, ethyl benzyl alcohol, phenethyl alcohol and other aromatic monohydric alcohols.

The most preferred co-solvent is benzyl alcohol. More preferably the benzyl alcohol is present in the range of 1–30% by weight.

Preferred vegetable oils are soya bean oil, sesame oil and corn oil.

The most preferred oil is soya bean oil.

Preferably the anthelmintic is chosen from the group comprising abamectin and ivermectin.

More preferably the abamectin or ivermectin is present in the range from 0.5–5% by weight of the formulation.

Optionally, a wetting agent such as ethyl oleate may be used to assist in dissolving the anthelmintic in solution.

Optionally, oil soluble vitamins may be added.

In another aspect the invention provides a solution suitable for oral administration containing an anthelmintic chosen from the class of macrocyclic lactones including but not limited to the avermectins, ivermectin, doramectin, abamectin, milbemycin, and moxidectin, together with a vegetable oil and a co-solvent chosen from the group comprising alcohols having 4 or more carbon atoms.

Preferred alcohols are benzyl alcohol, ethyl benzyl alcohol, phenethyl alcohol and other aromatic monohydric alcohols.

The most preferred co-solvent is benzyl alcohol. More preferably the benzyl alcohol is present in the range of 1–30% by weight.

Preferred vegetable oils are soya bean oil, sesame oil and corn oil.

The most preferred oil is corn oil.

Preferably the anthelmintic is chosen from the group comprising abamectin and ivermectin.

More preferably the abamectin or ivermectin is present in the range from 0.1–10% by weight of the formulation.

Optionally, a wetting agent such as ethyl oleate may be used to assist in dissolving the anthelmintic in solution.

Optionally, oil soluble vitamins may be added.

DRAWINGS

FIG. 1: is a chart showing Faecal Egg Counts prior to treatment and for two weeks after treatment (Trial 1).

Figure 2:
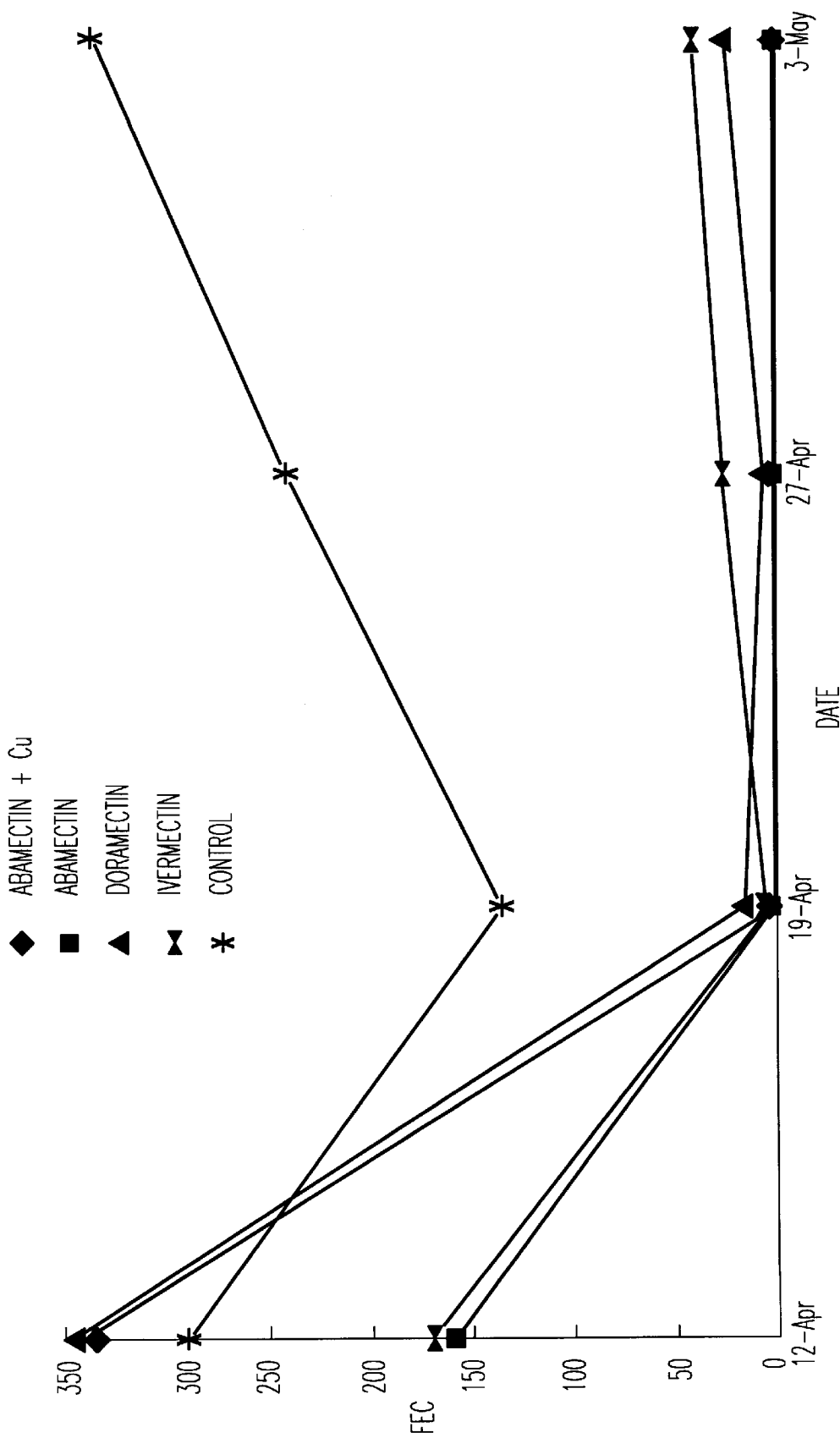

FIG. 2: is a chart showing Faecal Egg Counts prior to treatment and for three weeks after treatment (Trial 2).

DEFINITIONS

| | |
|---|---|
| FEC | stands for Faecal Egg Counts |
| FECR | stands for Faecal Egg Count Reduction |

PREFERRED EMBODIMENTS

These and other aspects of this invention, which should be considered and always novel aspects, will be apparent from the following examples.

We have found that the particular formulations of the chosen anthelmintic, as set out in the following examples, can increase the length of activity of the anthelmintic on external and internal parasites.

Avermectins, ivermectin, doramectin, abamectin, milbemycin and moxidectin oxidise and break down in water. Previous formulations of avermectin and ivermectin have been based on glycol solvents, glycerol formal, surfactants and/or water. These have had the disadvantage that the abamectin or ivermectin was rapidly released in the animal, giving a shorter activity which was also sometimes toxic. This resulted from the rapid absorption into the blood stream of the abamectin or ivermectin and excretion of the drug. It is particularly noted in the case of young animals, who have a low tolerance to these high levels of abamectin or ivermectin in the blood stream. Indeed, calves under ten weeks old cannot be treated with an injectable composition containing abamectin and a co-solvent as this may be toxic.

Avermectins, ivermectin, doramectin, abamectin, milbemycin and moxidectin are sparingly soluble in oils such as sesame oil, soya bean oil and corn oil. Pure sesame oil has a relatively high viscosity, which makes it unsuitable for use as a solvent for injection using typical veterinary syringes. We have found that by using sesame oil, soya bean oil or corn oil together with a co-solvent chosen from the class of alcohols having four or more carbon atoms, and more preferably benzyl alcohol it is possible to make a stable solution containing avermectins, ivermectin, doramectin, abamectin, milbemycin or moxidectin which allows the avermectins, ivermectin, doramectin, abamectin, milbemycin or moxidectin to remain in solution even when stored in cold conditions, whilst at the same time allowing the controlled release of the drug into the animal's body, for use against both internal and external parasites. Solutions can be prepared which are suitable for injection, pour-on application and/or oral administration.

Injectable Formulations:

Example 1:

| | | |
|---|---|---|
| | Ivermectin | 1% |
| | Benzyl Alcohol | 20% |
| | Sesame Oil | to 100% |

Example 2:

| | | |
|---|---|---|
| | Ivermectin | 1% |
| | Benzyl Alcohol | 20% |
| | Soya Bean Oil | to 100% |

Example 3: Trial Solution 1

| | | |
|---|---|---|
| | Abamectin | 1% |
| | Benzyl Alcohol | 20% |
| | Sesame Oil | to 100% |

The abamectin was dissolved in a mixture of benzyl alcohol and sesame oil.

Example 4:

| | | |
|---|---|---|
| | Ivermectin | 1% |
| | Benzyl Alcohol | 20% |
| | Soya Bean Oil | to 100% |

Example 5:

| | | |
|---|---|---|
| | Ivermectin | 1% |
| | Benzyl Alcohol | 20% |
| | Ethyl Oleate | 10% |
| | Sesame Oil | to 100% |

Example 6:

| | | |
|---|---|---|
| | Abamectin | 1% |
| | Benzyl Alcohol | 20% |
| | Ethyl Oleate | 10% |
| | Soya Bean Oil | to 100% |

Trial 1

Evaluation of the efficacy of Trial Solution 1 Injection in the control and treatment of naturally occurring infection with common pathogenic nematodes in cattle.

TRIAL ACTIVITY AND DESIGN

Day 1

Animals selected and allocated randomly:
15 cattle untreated control
100 cattle treated with Dectomax*
100 cattle treated with Trial Solution 1

Animals weighed

Samples taken for the FEC from 15 control animals and 15 animals in each treated group. Animals giving samples identified so that they can be followed throughout the trial.

Larval development test on group samples conducted.

Animals treated as per treatment protocol.

(*Dectomax is a registered trade mark of Pfizer Pty Limited)

Day 7

Samples for the FEC from each of 45 identified animals taken

If eggs are present in the faeces, conduct larval development test on group samples for confirmation of the species involved.

Day 14

Samples for the FEC from each of 45 identified animals taken.

If eggs are present in the faeces, conduct larval development test on group samples for confirmation of the species involved.

Some of the animals in the control group treated due to high egg counts. PARASITOLOGY ANALYSIS Faecal samples will be analysed for gastrointestinal nematodes and lungworms. Larval differentiation test will also be performed whenever the eggs are present. Only initial larval differentiation results are available at the moment.

RESULTS

Mean FEC and % of reduction per group prior to treatment and for 2 weeks after the treatment:

| | Day 1 | Day 7 | Day 14 |
|---|---|---|---|
| abamectin | 490* | 0(100%) | 3.3(99.8%) |
| doramectin | 610* | 10.7(98.9%) | 350(86.8%) |
| control | 586* | 1056.6 | 1896.6 |

*no statistical difference between the treatment

FIG. 1 shows the graphical representation of these results.

Trial 2

Evaluation of the efficacy of Trial Solution 1 Injection in the control and treatment of naturally occurring infection with common pathogenic nematodes in cattle.

TRIAL ACTIVITY AND DESIGN

Day 1

Animals selected and allocated randomly:
100 cattle to each group:
C=controls
A=abamectin+copper injection
B=doramectin+copper injection
G=abamectin (Trial Solution 1)
I=ivermectin+copper injection Animals weighed.

Samples taken for the FEC.

Larval development test on group samples conducted.

Animals treated as per treatment protocol.

Day 7

Samples for the FEC taken.

Larval development test on group samples conducted.

Day 14

Samples for the FEC taken.

Larval development test on group samples conducted.

Day 21
Samples for the FEC taken.
Larval development tests on group samples conducted.

PARASITOLOGY ANALYSIS

Faecal samples were analysed for gastrointestinal nematodes and lungworms. Larval differentiation test were performed whenever the eggs are present.

RESULTS

Mean FEC and % of reduction per group prior to treatment and for 3 weeks after the treatment:

|  | Day 1 | Day 7 | Day 14 | Day 21 |
| --- | --- | --- | --- | --- |
| abamectin+Cu | 340 | 0(100%) | 0(100%) | 0(100%) |
| abamectin | 160 | 0(100%) | 0(100%) | 0(100%) |
| doramectin | 345 | 15(88.88%) | 5(97.91%) | 25(92.53%) |
| ivermectin | 170 | 5(96.29%) | 25(89.58%) | 40(88.05%) |
| control | 290 | 135 | 240 | 335 |

FIG. 2 shows the graphical representation of these results.

Trial 3

A trial was undertaken to assess the efficacy of Trial Solution 1 injection and Stand-by pour-on formulations against natural infections of gastro-intestinal nematode parasites of cattle. Twenty-four clinically healthy Friesian and Friesian cross male calves, 6–7 months of age, and of similar body condition, harbouring natural infections were restrictively randomised into 4 groups. Group 1 remain as the untreated control, Group 2 was injected subcutaneously in the left side of the neck with Abamectin L A (200 $\mu$g/kg), Group 3 was treated with the Stand-by pour-on formulation along the mid line of the back and Group 4 was treated with Ivomec* Pour-on formulation (500 $\mu$g/kg) in accordance with the manufacturers recommendation (MSD AgVet). On days 7 and 8 post treatment the calves were necropsied for worm counts. At necropsy all the treated groups harboured significantly fewer adult, late $4^{th}$ and early $4^{th}$ stage worms of the main cattle parasites viz. Ostertagia spp. and Cooperia spp. as well as *Haemonchus contortus* ($p<0.01$). Only in the case of Cooperia spp was there a significant difference between treated groups there being fewer adult worms present in the group treated with injectable abamectin ($p<0.01$). There were also significantly fewer adult and late $4^{th}$ stage worms of *Trichostrongylus axei* in the treated groups but not early $4^{th}$ stage worms. All three treated groups also showed significant efficacy against adult *Dictyocaulus viviparus, Chabertia ovina* (both $p<0.01$), Capillaria spp. and Trichuris spp. (both $p<0.05$).

(*Ivomec is a registered trade mark of Merck & Co., Inc. and is used on compositions containing ivermectin)

No adverse reactions to the treatments were observed at the time of their administration. There were no visible lesions at the injection site of Group 2 calves at slaughter 7 days after treatment.

Experimental Procedures

Animals: Twenty four clinically healthy Friesian and Friesian cross male calves, 6–7 months of age, and of similar body condition, harbouring natural infections of gastrointestinal nematodes were obtained from commercial properties and held on pasture for 7 days prior to the commencement of the trial. The calves were individually identified by ear tags on arrival at Wallaceville Animal Research Centre, weighed and sampled for faecal egg counts to ensure they were carrying adequate worm burdens.

Animal Welfare: Animals handling procedures were in compliance with local regulations and conducted with the approval of the Wallaceville Animal Ethics Committee—AEC No. 440.

Parasite burdens: On arrival on day-7 the animals were weighed and faecal sampled and a bulk faecal culture was undertaken to identify the composition of the calves worm burdens.

Treatments: On Day 0 the calves were re-weighed and randomly allocated to four treatment groups on the basis of faecal egg count, live weight and overall body condition (see Table 1). Treatments were administered according to individual live weights using disposable 5.0, 10.0 or 20.0 ml graduated plastic syringes (see Appendix 2 Table 1b). Group 2 was injected in the left side of the neck near the base of the ear with Abamectin L.A. (200 $\mu$g/kg); Group 3 was treated with the Stand-by Pour-on formulation (500 $\mu$g/kg MSD Ag Vet) in accordance with the manufacturer's recommendation and Group 1 remained as the untreated control.

TABLE 1

Treatment Allocation

| Group | Count | Anthelmintic | Dose/Kg |
| --- | --- | --- | --- |
| 1 | n = 6 | Untreated Control | — |
| 2 | n = 6 | Abamectin injectable Day 0 | 200$\mu$g/kg |
| 3 | n = 6 | Stand-by pour-on Day 0 | |
| 4 | n = 6 | Ivomec Pour-on Day 0 | 500$\mu$g/kg |

Husbandry—Feed and water: The animals were maintained on pasture for the duration of the trial with ready access to drinking water. The groups treated with pour-on anthelmintics were kept on separate pastures for approximately 12 hours after treatment to avoid the transfer of the pour-on formulations to those in other groups. At all other times the calves were maintained as one herd.

Reactions to treatments: All animals were observed for adverse reactions to the anthelmintics immediately after treatment and when they were returned to pasture. At time of slaughter Group 2 calves (Abamectin injectable) had the left side of the neck skinned in order to assess any reaction to the treatment.

Faecal Sampling: All animals were faecal sampled on Day-7, Day 0 and Day 5. Faecal egg counts were carried out using a modified McMaster technique in which each egg counted represents 50 eggs per gram faeces.

Necropsies: The calves were necropsied on Days 7 and 8 following anthelmintic treatment. The groups were arbitrarily divided into two with half of each group slaughtered on each day. The animals were euthanased by stunning with a captive bolt pistol followed by ex-sanguination and severing of the nerve chord. Worm counts of the gastro intestinal tracts and lungs were carried out using the method described by Brunsdon, (1972) and in accordance with the World Association for the Advancement of Veterinary Parasitology guidelines (Wood et al. (1995)). Lungs and the abomasal mucosa were processed using the techniques described by Downey (1981) and Oakley (1989).

Briefly the lungs together with the heart and the gastrointestinal tract were removed and the abomasum, small intestine and large intestine ligatured and separated. The lungs were infused after the method of Oakley (1989) using mains pressure water directed through the pulmonary artery.

Approximately 8 liters were passed through each lung. The bronchial tree was then opened with scissors and examined to ensure no worms remained. The total contents and washings of the abomasum and small intestine were also collected separately, made up to 8 liters and a 1/10 aliquot passed through a 45μ sieve and preserved with formalin for counting. The contents and washings of the abomasum and small intestine were also collected separately, made up to 8 liters and a 1/10 aliquot passed through a 45μ sieve and preserved with formalin for counting. The contents of the large intestine were made up to 8 liters and half passed through 635μ sieve and preserved with formalin for counting. The abomasal mucosa of each animal was incubated in 1.5 liters of physiological saline at 37° C. over night (Downey, 1981) and then treated as with the contents.

Nematode Counts: Nematodes present in the total contents of the washings from the lungs, the ½ aliquot sample of the large intestine, a ⅕ subsample of the abomasal contents, abomasal mucosa and a 1/10 subsample of the small intestine were identified to developmental stage and genus and counted. Counts were multiplied by the appropriate aliquot factor to give total numbers present in each organ. The first 20 adult male worms of the genera Ostertagia and Cooperia in each sample (depending on availability) were identified to species using the spicule morphology to determine the species composition of the respective worm population on a proportional basis.

Statistical Methods: Data for both faecal egg counts and worm counts were transformed to Loge(X+100) to normalise their distributions before analyses were carried out. FEC's and worm counts were analysed by 1-way ANOVA's using the Minitab 10.5 statistical package. FEC's and worm counts given in tables are the back transformed values. The percentage efficacy were calculated as:

(Mean of Control—Mean of Treatment/Mean of Control)×100

Results:

Faecal culture:

Results of the pre-treatment faecal culture indicated that the following genera of gastrointestinal nematodes were present in the experimental herd—*Haemonchus contortus*, Ostertagia spp., Trichostrongylus spp., Cooperia spp., and Oesophagostomum spp. (Table 2).

Table 2: Generic composition of faecal egg output of trial animals pre-treatment.

| Genus | L3 - Count | Percent |
|---|---|---|
| Trichostrongylus spp | 5 | 2 |
| Ostertagia spp. | 23 | 12 |
| Haemonchus contortus | 6 | 3 |
| Cooperia spp | 162 | 81 |
| Oesophagostomum spp | 4 | 2 |
| Total | 200 | 100 |

Faecal egg counts (FEC's)

Pre- and post- treatment FEC's and percentage faecal egg count reductions (FECR) are presented in Table 3. FEC's of all three treated groups of day 5 were significantly lower than the controls (p<0.01) but not significantly different from one another. The FECR for the injectable formulation of abamectin was the higher than both of the pour-on treatments.

Table 3: Faecal Egg Counts (Geometric means).

| | Pre-treatment | | Post-treatment | |
|---|---|---|---|---|
| Group | FEC 1 - 8/02 | FEC 2 - 15/02 | FEC 3 - 20/02 | FECR % |
| 1 Control | 546.0 | 733.3 | 673.7[a] | |
| 2 Abamec LA | 537.9 | 393.9 | 6.9[b] | 98.97 |
| 3 Stand-by P-on | 513.7 | 528.9 | 46.8[b] | 93.05 |
| 4 Ivomec P-on | 568.1 | 641.6 | 54.3[b] | 91.94 |

FECR = Faecal egg count reduction for FEC3 on samples taken 5 days post treatment. Values for FEC 3 for 20/02 with different super scripts are significantly different (p < 0.01).

Worm counts

The geometric mean worm burdens recovered from the abomasum, small intestine, large intestine and the lungs and the percentage reduction are presented in Tables 4–7. A small number of parasites of sheep origin were present in the calves which had been in a mixed grazing management system. Treated animals had significantly fewer adult, late 4th and early 4th stage worms of Ostertagia spp, *Haemonchus contortus*, and Cooperia spp. Only in the case of Cooperia spp was there a difference between treatment groups there being significantly fewer adult and late 4th stage worms of *Trichostrongylus axei* in all treated groups but not early 4th stage larvae. Due to the trial design it cannot be verified that this is due to the lower efficacy of the treatments against this developmental stage at the calves may have acquired some larvae while grazing on pasture between the treatment date and the time of their slaughter. All three treatments also showed significant efficacy against adult *Dictyocaulus viviparus, Chabertia ovina* (both p<0.01) as well as Capillaria spp. and Trichuris spp. (both p<0.05). The efficacy of the treatments against a Nematodirus spp., and Oesophagostomum spp. could not be determined with any degree of accuracy as there were only present in small numbers.

TABLE 4

Mean abomasal worm burdens (Geometric data).

Mean worm count and % efficacy for treatment groups

| Genus & stage of development | Group 1 | Group 2 | Group 3 | Group 4 |
|---|---|---|---|---|
| Ostertagia spp Adult (5th) | 6921.2[a] | 33.4[b] (99.5) | 6.9[b] (99.9) | 6.9[b] (99.9) |
| Late 4th | 466.9[a] | 6.9[b] (98.5) | 24.6[b] (94.7) | 6.9[b] (98.5) |
| Early 4th | 1837.6[a] | 34.8[b] (98.1) | 44.2[b] (97.6) | 35.7[b] (98.1) |
| Trichostrongylus axei Adult | 3529.7[a] | 20.1[b] (99.4) | 23.2[b] (99.3) | 81.7[b] (97.5) |
| Late 4th | 1087.7[a] | 20.1[b] (98.2) | 28.5[b] (97.4) | 61.9[b] (94.3) |
| Early 4th | 3252.6 | 822.5 (74.7) | 1023.2 (68.5) | 1614.2 (50.4) |
| Haemonchus contortus Adult (5th) | 277.1[a] | 0.0[b] (100) | 0.0[b] (100) | 0.0[b] (100) |
| Late 4th | 312.3[a] | 0.0[b] (100) | 28.5[b] (90.9) | 0.0[b] (100) |

TABLE 4-continued

Mean abomasal worm burdens (Geometric data).

Mean worm count and % efficacy for treatment groups

| Genus & stage of development | Group 1 | Group 2 | Group 3 | Group 4 |
|---|---|---|---|---|
| Early 4th | 1360.3[a] | 49.7[b] (96.3) | 54.3[b] (96.0) | 39.9[b] (97.1) |

For rows values with different super scripts are significantly different (p < 0.01).

TABLE 5

Mean small intestinal worm burdens (Geometric data).

Mean worm count and % efficacy for treatment groups

| Genus & stage of development | Group 1 | Group 2 | Group 3 | Group 4 |
|---|---|---|---|---|
| Cooperia spp Adult (5th) | 51434.2[a] | 248.6[c] (99.5) | 3479.6[b] (93.2) | 3055.8[b] (94.1) |
| Late 4th | 7398.1[a] | 0.0[b] (100) | 84.9[b] (98.8) | 49.1[b] (99.3) |
| Early 4th | 23216.4[a] | 243.1[b] (98.9) | 465.1[b] (98.0) | 462.3[b] (98.0) |
| Thichostrongylus spp Adult (5th) | 15.1 | 0.0 | 0.0 | 0.0 |
| Late 4th | 12.2 | 0.0 | 0.0 | 0.0 |
| Early 4th | 30.8 | 0.0 | 0.0 | 0.0 |
| Nematodirus spp Adult (5th) | 453.4 | 0.0 | 195.9 | 159.6 |
| Capiliaria spp Adult (5th) | 70.1[x] | 0.0[y] | 0.0[y] | 12.2[y] |

For rows values with different super scripts are significantly different a, b (p < 0.01); x, y (p < 0.05). Rows with non-annotated values are not significantly different.

TABLE 6

Mean large intestinal worm burdens (Geometric data).

Mean worm count and % efficacy for treatment groups

| Genus & stage of development | Group 1 | Group 2 | Group 3 | Group 4 |
|---|---|---|---|---|
| Oesophagostomum Adult (5th) | 1.3 | 0.0 | 0.0 | 0.0 |
| Trichuris spp Adult (5th) | 24.8[x] | 0.0[y] | 2.3[y] | 1.3[y] |
| Chabertia ovina Adult (5th) | 1.0[a] | 0.0[b] | 0.0[b] | 0.0[b] |

For rows values with different super scripts are significantly different a, b (p < 0.01); x, y (p < 0.05).

TABLE 7

Mean lungworm burdens (Geometric data).

Mean worm count and % efficacy for treatment groups

| Genus & stage of development | Group 1 | Group 2 | Group 3 | Group 4 |
|---|---|---|---|---|
| Dictyocaulus viviparus Early 5th adults | 10.9[a] | 0.0[b] (100) | 0.0[b] (100) | 0.0[b] (100) |

Values with different super scripts are significantly different (p < 0.01).

Species composition (Ostertagia and Cooperia).

Four species of Ostertagia and three species of Cooperia were identified from the worm burdens of the calves in the trial—i.e. *O. ostertagi, O. lyrata, O. leptospicularis, O. kolchida, C. oncophora, C. mcmasteri*, and *C. punctata. O. ostertagi* and *C. oncophora* were the predominant species present representing approximately 60% and 75% of the respective genera (Table 8). All three anthelmintic treatments appeared equally effective against all species of Ostertagia and similar proportions of all Cooperia species remained after treatment.

Table 8: Species composition of the Ostertagia and Cooperia worm populations (based on the identification of adult males).

Mean % species composition and range

| Species | Group 1 | Group 2 | Group 3 | Group 4 |
|---|---|---|---|---|
| O. ostertagi | 60.2 (45–80) | * | * | * |
| O. lyrata | 27.6 (10–45) | * | * | ** |
| O. leptospicularis | 6.5 (0.10) | * | * | * |
| O. kolchida | 5.7 (0–10) | * | * | * |
| O. oncophora | 74.4 (61–80) | 77.0 (75–78) | 75.0 (67–80) | 78.3 (70–88) |
| O. mcmasteri | 10.1 (4–28) | 15.4 (0–22) | 13.8 (0–29) | 13.3 (9–18) |
| O. punctata | 15.5 (5–30) | 7.6 (0–25) | 11.2 (0–33) | 8.4 (0–15) |

\* = No adult males found
\*\* = Only adult male found

Injection sites

No adverse reaction to either the injectable or pour-on formulations was observed at the time of treatment. At the time of slaughter the injection sites of group 2 calves were examined by removing the skin from the neck of each animal. No reactions to treatment were found.

We have found that we can produce long acting injectable solutions containing between 0.5–5% of an anthelmintic chosen from the class of monocyclic lactones including but not limited to avermectins, ivermectin, doramectin, abamectin, milbemycin, and moxidectin, by using from 1–30% benzyl alcohol and a vegetable oil such as sesame oil or soya bean oil, and by optionally using from 5–30% of a wetting agent such as ethyl oleate. Optionally, oil soluble vitamins such as Vitamins A, D, E and $K_1$ may be added.

Oral Formulations:

Example 6:

| | | |
|---|---|---|
| | Ivemectin | 0.1% |
| | Benzyl Alcohol | 10% |
| | Corn Oil | to 100% |

Example 7:

| | | |
|---|---|---|
| | Abamectin | 0.1% |
| | Benzyl Alcohol | 10% |
| | Corn Oil | to 100% |

Example 8:

| | | |
|---|---|---|
| | Doramectin | 0.1% |
| | Benzyl Alcohol | 10% |
| | Corn Oil | to 100% |

Example 9:

| | | |
|---|---|---|
| | Milbemycin | 0.1% |
| | Benzyl Alcohol | 10% |
| | Corn Oil | to 100% |

We have found that we can produce long acting solutions for oral administration containing between 0.1–5% of an anthelmintic chosen from the class of monocyclic lactones including but not limited to avermectins, ivermectin, doramectin, abamectin, milbemycin, and moxidectin, by using from 1–30% benzyl alcohol and a vegetable oil such as corn oil, sesame oil or soya bean oil, and by optionally using from 5–30% of a wetting agent such as ethyl oleate. Optionally, oil soluble vitamins such as Vitamins A, D, E and $K_1$ may be added.

Pour-on Formulations:

Example 13:

| | | |
|---|---|---|
| | Abamectin | 1.0% |
| | Benzyl Alcohol | 20% |
| | Soya Bean Oil | to 100% |

Example 14:

| | | |
|---|---|---|
| | Ivermectin | 1.0% |
| | Benzyl Alcohol | 20% |
| | Soya Bean Oil | to 100% |

Example 15:

| | | |
|---|---|---|
| | Moxidectin | 1.0% |
| | Benzyl Alcohol | 20% |
| | Soya Bean Oil | to 100% |

Example 16:

| | | |
|---|---|---|
| | Abamectin | 1.0% |
| | Benzyl Alcohol | 20% |
| | Ethyl Oleate | 10% |
| | Soya Bean Oil | to 100% |

We have found that we can produce long acting pour-on solutions containing between 0.5–5% of an anthelmintic chosen from the class of monocyclic lactones including but not limited to avermectins, ivermectin, doramectin, abamectin, milbemycin, and moxidectin, by using from 1–30% benzyl alcohol and a vegetable oil such as sesame oil or soya bean oil, and by optionally using from 5–30% of a wetting agent such as ethyl oleate. Optionally, oil soluble vitamins such as Vitamins A, D, E and $K_1$ may be added.

ADVANTAGES

The relatively high viscosity of vegetable oils such as sesame oil makes them unsuitable for use as a solvent for injection using typical veterinary syringes. However, a co-solvent chosen from the class of alcohols having 4 or more carbon atoms, and preferably benzyl alcohol, decreases the viscosity of the vegetable oil such that the vegetable oil becomes a suitable solvent for injection.

The active anthelmintic ingredient remains in solution in formulations of this invention even when stored for long periods or in cold conditions.

The formulations of this invention also allow the controlled release of the active anthelmintic in the blood stream of the animal.

INDUSTRIAL APPLICATION

The formulations shown above are effective in the treatment of helmithiasis in cattle and other domestically important animals including, but not limited to, goats and pigs.

VARIATIONS

Whilst the above examples have concentrated on the use of ivermectin and abamectin, it will be appreciated that the same technique can be used to provide stable formulations for injectable, pour-on or oral administration containing an anthelmintic chosen from the group comprising avermectins, ivermectin, doramectin, abamectin, milbemycin, and moxidectin.

Although we prefer to use sesame oil in these formulations other vegetable oils such as soya bean oil, corn oil and rape oil are possible as are other viscous vegetable oils.

Benzyl alcohol is the preferred co-solvent, however other co-solvents may be used in some formulations.

Finally it will be appreciated that various other alterations and modifications may be made to the forgoing without departing from the spirit or scope of this invention.

REFERENCES

Brunsdon. R. V., 1972: Inhibited development of Ostertagia spp. and Cooperia spp. in naturally acquired infection in calves. *N.Z. Veterinary Journal* 20: 183–189)

Downey, N. E., 1981: Recovery of Ostertagia from bovine abomasal mucosa by immersion in warm normal saline. In P. Nansen, R. J. Jorgenson, E. J. L. Soulsby, Eds Epidemiology and Control of Nematodiasis in Cattle. *ECSC, EAEC, Brussels Luxembourg.*

Oakley, G. A., 1989: The recovery of *Dictycaulus viviparous* from bovine lungs by lung perfusion: a modification of Inderbitzern's method. *Research in Veterinary Science.* 29, 395–6.

Wood I. B., Amaral N. K., Bairden K. et al. 1995: World Association for the Advancement of Veterinary Parasitology (W.A.A.V.P)—Second Edition of Guidelines for Evaluating the Efficacy of Anthelmintics in Ruminants (bovine, ovine, caprine). *Veterinary Parasitology* 58: 181–213.

I claim:

1. An anthelmintic composition comprising: an anthelmintic compound selected from the class of macrocyclic lactones, together with a vegetable oil and a co-solvent selected from the group consisting of alcohols having 4 or more carbon atoms.

2. The composition of claim 1, wherein the anthelmintic compound is selected from the group consisting of the avermectins, ivermectin, doramectin, abamectin, milbemycin, and moxidectin.

3. The composition of claim 1, wherein the co-solvent is selected from the group consisting of benzyl alcohol, ethyl benzyl alcohol, phenethyl alcohol, and other aromatic monohydric alcohols.

4. The composition of claim 3, wherein the co-solvent is benzyl alcohol.

5. The composition of claim 4, wherein the benzyl alcohol is present in the range of 1–30% by weight.

6. The composition of claim 1 wherein the vegetable oil is selected from the group consisting of sesame oil, soya bean oil, and corn oil.

7. The composition of claim 1 wherein the anthelmintic compound is present in the range of from 0.1–5% by weight of the formulation.

8. A method of treating helminthiasis by injecting an animal with a composition as claimed in claim 1 at the rate of 100–300 µg/kg of the animal's live weight.

9. A method of treating helminthiasis by applying a topical pour-on composition as claimed in claim 1 at the rate of 200–600 µg/kg of the animal's live weight.

10. A method of treating helminthiasis by drenching an animal with a composition as claimed in claim 1 at the rate of 100–300 µg/kg of the animal's live weight.

\* \* \* \* \*